United States Patent
Khouri et al.

(10) Patent No.: US 6,919,418 B2
(45) Date of Patent: Jul. 19, 2005

(54) APPROACH TO REDUCE CYCLICS FORMATION IN 3-CIPA BASED POLYETHERIMIDE POLYMERS

(76) Inventors: Farid Fouad Khouri, 6 Tamarack La., Clifton Park, NY (US) 12065; Daniel Joseph Brunelle, 4 Woods Edge, Burnt Hills, NY (US) 12027; Donald Scott Johnson, 91 St. Stephens La., Scotia, NY (US) 12302

( * ) Notice: Subject to any disclaimer, the term of this patent is extended or adjusted under 35 U.S.C. 154(b) by 0 days.

(21) Appl. No.: 10/647,679

(22) Filed: Aug. 25, 2003

(65) Prior Publication Data

US 2005/0049384 A1 Mar. 3, 2005

(51) Int. Cl.$^7$ .................. C08G 73/10; C08G 69/26; C08G 65/40; C07D 209/00
(52) U.S. Cl. .................. 528/170; 528/125; 528/126; 528/128; 528/171; 528/172; 528/173; 528/174; 528/176; 528/179; 528/183; 528/185; 528/188; 528/220; 528/229; 528/350; 528/352; 528/353; 525/420; 525/422; 525/432; 525/436; 546/256; 546/304
(58) Field of Search .................. 528/170, 125–126, 528/128, 171–174, 176, 179, 183, 185, 188, 220, 214, 216, 219, 229, 350, 353, 352; 525/436, 439, 420, 422, 432; 546/256, 304

(56) References Cited

U.S. PATENT DOCUMENTS

| 4,217,438 A | | 8/1980 | Brunelle et al. | |
|---|---|---|---|---|
| 4,988,544 A | * | 1/1991 | Cella et al. | 427/384 |
| 5,229,482 A | | 7/1993 | Brunelle | |
| 5,830,974 A | | 11/1998 | Schmidhauser et al. | |
| 5,908,915 A | * | 6/1999 | Brunelle | 528/170 |
| 5,917,005 A | * | 6/1999 | Brunelle et al. | 528/353 |
| 6,020,456 A | * | 2/2000 | Brunelle et al. | 528/353 |
| 6,235,866 B1 | * | 5/2001 | Khouri et al. | 528/125 |

FOREIGN PATENT DOCUMENTS

EP 0 892 003 1/1999

OTHER PUBLICATIONS

PCT Search Report—Oct. 22, 2004.

* cited by examiner

Primary Examiner—P. Hampton Hightower
(74) Attorney, Agent, or Firm—Carter, DeLuca, Farrell & Schmidt, LLP

(57) ABSTRACT

Methods of reducing the amount of undesirable cyclic oligomer by-products in the production of polyetherimides are disclosed. The resulting polyetherimides have enhanced thermomechanical properties.

26 Claims, 2 Drawing Sheets

APPROACH TO REDUCE CYCLICS FORMATION IN 3-CIPA BASED POLYETHERIMIDE POLYMERS

BACKGROUND OF THE INVENTION

The present disclosure is directed to methods for reducing the levels of cyclic oligomers produced during the formation of polyetherimide resins. More particularly, sterically hindered substituted aromatic diamines are utilized which result in lower formation of undesirable cyclic oligomer by-products. Polyetherimides produced in accordance with the methods disclosed herein are also provided.

Aromatic polyethers, particularly polyetherimides, are important engineering resins because of their excellent properties. One route for the synthesis of these polymers is by the reaction of salts of dihydroxyaromatic compounds, such as bisphenol A disodium salt (BPA.Na$_2$), with dihaloaromatic molecules. For example, polyetherimides are conveniently prepared by the reaction of salts of dihydroxyaromatic compounds with bis(halophthalimides) as illustrated by 1,3-bis[N-(4-chlorophthalimido)]benzene (hereinafter sometimes "ClPAMI"), which has the structure:

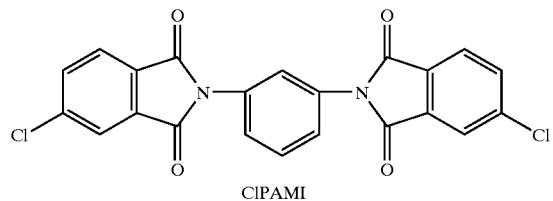

ClPAMI
(I)

The bis(halophthalimides), in turn, are frequently produced by reacting at least one diamino compound, preferably an aromatic diamine such as m-phenylenediamine (mPD) or p-phenylenediamine (pPD), and at least one halophthalic anhydride such as 3-chlorophthalic anhydride (3-ClPA), 4-chlorophthalic anhydride (4-ClPA), dichlorophthalic anhydride, or mixtures thereof.

According to U.S. Pat. Nos. 5,229,482 and 5,830,974, the preparation of aromatic polyethers may be conducted in solution in relatively non-polar solvents, using a phase transfer catalyst which is substantially stable under the temperature conditions employed. Solvents disclosed in U.S. Pat. No. 5,229,482 include o-dichlorobenzene, dichlorotoluene, 1,2,4-trichlorobenzene and diphenyl sulfone. In U.S. Pat. No. 5,830,974, monoalkoxybenzenes such as anisole, diphenylether, or phenetole are employed. Solvents of the same types may be used for the preparation of the bis(halophthalimide) intermediates.

The polyetherimides produced by these displacement polymerizations have a relatively high polydispersivity, ranging from about 2.6 to about 3.6, depending upon the amount of 3-ClPA and 4-ClPA used in preparing the ClPAMI monomer. The general scheme for the production of bis(halophthalimide) and the subsequent production of polyetherimide is set forth in FIG. 1.

When bisphenol A, mPD and 4-ClPA are used to produce polyetherimides, it has been found that the level of cyclic oligomers in the final product is about 3%. However, it has been found that the amount of cyclics increases as the level of 3-ClPA is increased as a starting material in ClPAMI synthesis. Where 100% 3-ClPA and mPD are used as the starting material, the amount of cyclic oligomers can range from about 15% to about 20%. Interestingly, it has been found that about two thirds of the cyclic oligomers are a single 1:1 adduct. The reaction scheme demonstrating the use of 3-ClPAMI to produce a polyetherimide with the cyclic oligomer by-product is set forth in FIG. 2.

High levels of these cyclic oligomers can have adverse effects on the properties of the resulting polymer. Such negative effects include a lower glass transition temperature (Tg), reduced ductility, and problems with processing including surface appearance, as demonstrated by reduced glossiness.

In addition, the cyclic by-products, being off specification, must be discarded after separation, increasing the cost and size of the waste stream and reducing the efficiency of the process.

However, it has also been found that the use of 3-ClPA in combination with other bisphenols and diamines can produce polyetherimides possessing higher Tg (about 15° to about 20° C. higher), and improved flow at high shear. It is therefore desirable to use 3-ClPA as a starting material, at least in part, in the production of polyetherimides, but means for reducing the levels of cyclic oligomers are desirable.

BRIEF DESCRIPTION OF THE INVENTION

The present disclosure provides a method for producing bis(phthalimides) which, in turn, may be utilized to produce polyetherimide resins with decreased amounts of undesirable cyclic oligomer by-products.

In one of its aspects, the present disclosure includes methods for producing a bis(halophthalimide) which comprises combining at a temperature of at least 110° C.:

at least one halophthalic anhydride;

a 1,3-diamine having at least one substituent ortho to one of its amine functionalities; and an organic liquid having a polarity no higher than that of o-dichlorobenzene, dichlorotoluene, 1,2,4-trichlorobenzene, diphenyl sulfone, anisole and veratrole.

In one embodiment, an imidization catalyst is added to enhance production of the bis(halophthalimide).

In another embodiment, the bis(halophthalimide) is a bis[N-(3-chlorophtalimide)] derivative of a diamine made by contacting at a temperature of at least 110° C. a 3-chlorophthalic anhydride with a 1,3-diamine having at least one substituent ortho to one of its amine functionalities in the presence of an organic liquid having a polarity no higher than that of o-dichlorobenzene, dichlorotoluene, 1,2, 4-trichlorobenzene, diphenyl sulfone, anisole and veratrole. In some embodiments the bis[N-(3-chlorophthalimide)] derivative can be 2,4-bis[N-(3-chlorophthalimido)]toluene, 2,6-bis[N-(3-chlorophthalimido)]toluene, 2,4-bis[N-(3-chlorophthalimido)]-3,5-diethyltoluene, or 2,6-bis[N-(3-chlorophthalimido)]-3,5-diethyl toluene.

Another aspect of the present disclosure is directed to methods for preparing polyetherimides by combining the above bis(halophthalimides) with at least one alkali metal salt of a dihydroxy-substituted aromatic compound in the presence of a phase transfer catalyst. Preferably, the polyetherimides so produced have low levels of undesirable cyclic oligomer by-products.

DETAILED DESCRIPTION OF THE INVENTION

Figure 1:
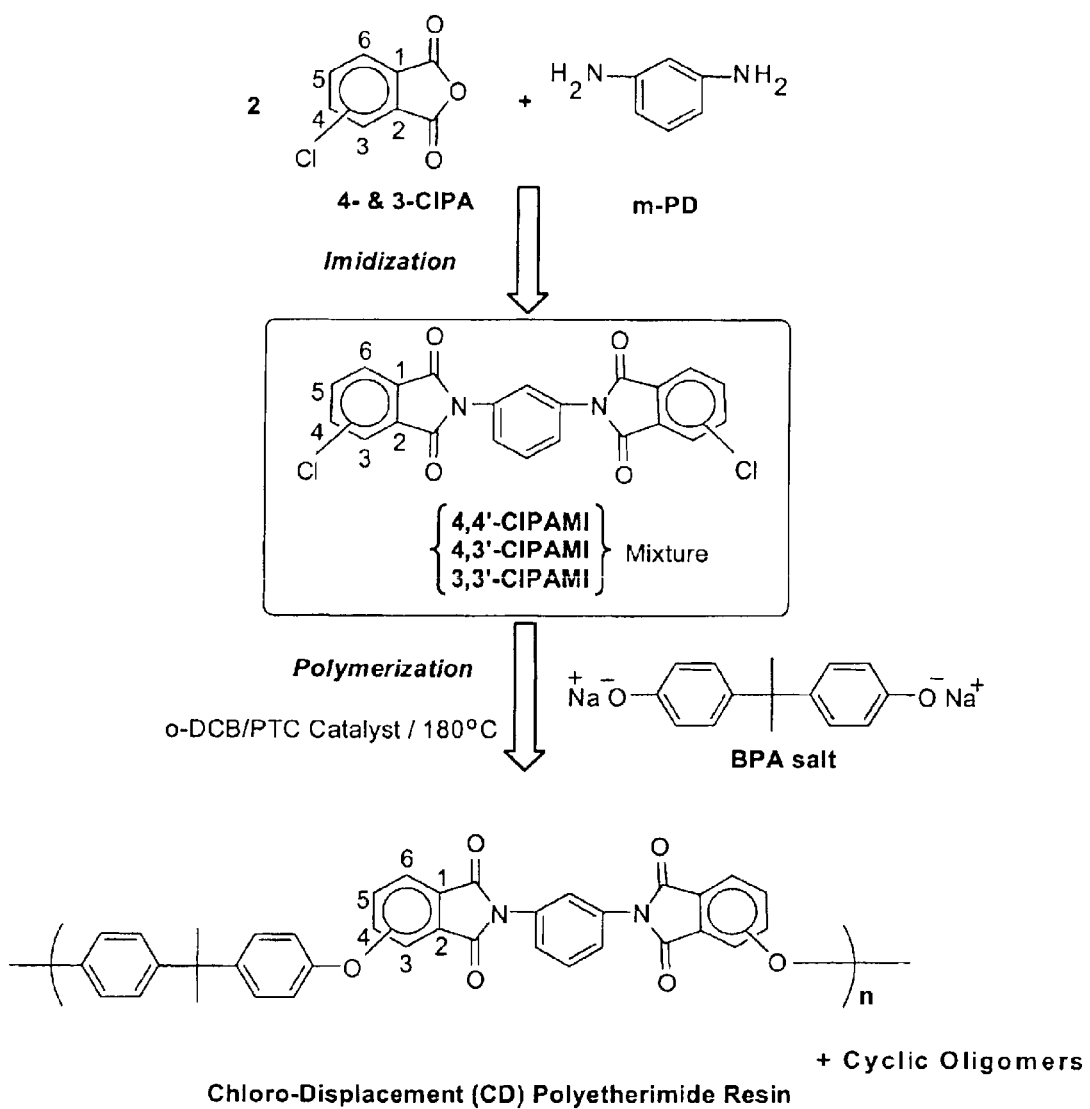
FIG. 1 is an overview of the ClPAMI and polyetherimide synthesis process.
Figure 2:
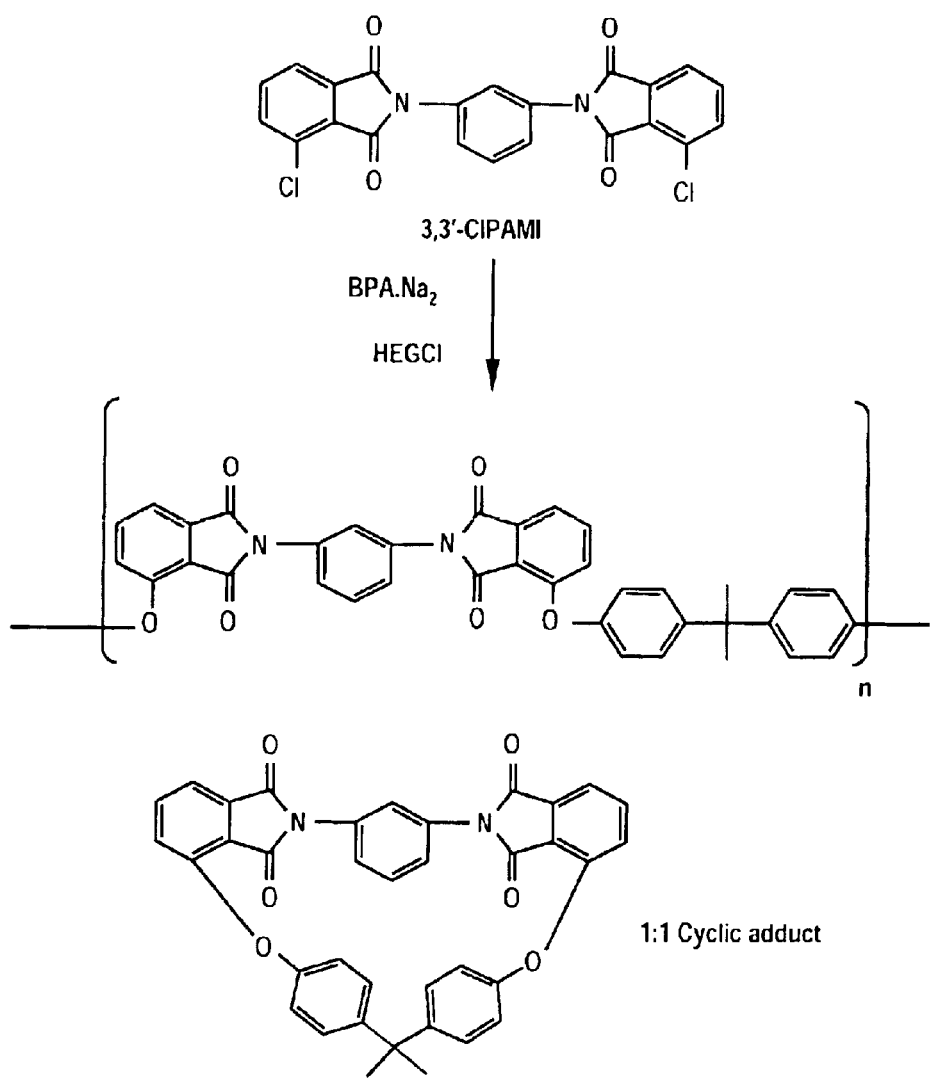
FIG. 2 is a depiction of ClPAMI synthesis demonstrating undesirable cyclic formation.

In accordance with the methods of the present disclosure, it has been surprisingly found that levels of cyclic oligomers produced during the polymerization reaction of bisphenol A disodium salt and a ClPAMI monomer may be reduced by utilizing diamines other than mPD in the formation of ClPAMI.

Anhydrides suitable for use in the present invention have formula (II)

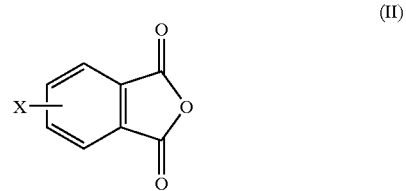

(II)

wherein X is a moiety which may be any organic group that does not interfere with the reaction. In one embodiment X is a displaceable group which participates in a subsequent polymerization reaction. Preferably, X is nitro, nitroso, tosyloxy (-OTs) or halogen; most preferably X is chlorine. Especially preferred anhydrides include 3-chlorophthalic anhydride, 4-chlorophthalic anhydride, and dichlorophthalic anhydride. In a most preferred embodiment, the ClPAMI monomer is made from either substantially pure 3-ClPA or a mixture of 3-ClPA combined with other phthalic anhydride monomers selected from the group consisting of 4-chlorophthalic anhydride, dichlorophthalic anhydride, and substituted analogs thereof where the other positions on the aromatic ring of the anhydride are either hydrogen atoms or substituted with nonreactive groups such as alkyl or aryl groups, and mixtures thereof.

In addition, in one embodiment of the present disclosure, phthalic anhydride (i.e., a compound having the structure of formula (II) wherein X is hydrogen) may be separately added to the reaction mixture. In such a case, the addition of phthalic anhydride to the reaction mixture will provide a mixture comprising both polymerizable monomer and end-capping monomer, i.e., a halophthalimide having only one reactive site which is thus capable of end-capping a growing polymer chain in a polymerization reaction. In such a case, the use of phthalic anhydride to form end-capping monomers may be used to control the molecular weight of the polyetherimide produced in the subsequent polymerization reaction. In addition, as known to those skilled in the art, other anhydrides may be utilized to form end-capping monomers.

In accordance with the present disclosure, it has been surprisingly found that the use of 1,3-diamines that have at least one substituent ortho to one of the amine functionalities can be used to make ClPAMI monomers capable of reacting with BPA disodium salt to provide polymers with reduced levels of undesirable cyclic oligomer by-products. These diamines are commercially available and are relatively inexpensive. Preferred diamines have the following structure (III):

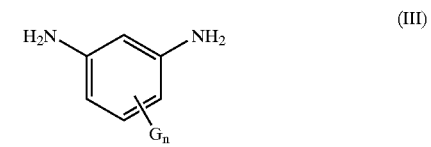

(III)

where n is 1 to 4 and G can be any group that is stable at high temperatures and is compatible with phenoxide displacement polymerization. Examples of G include, but are not limited to, —R, —OR, —SR, —Ar, —OAr, —SAr, —CN etc.

Suitable R groups include, but are not limited to, $C_1$ to $C_{30}$ aliphatic hydrocarbons, $C_1$ to $C_{30}$ unsaturated cycloaliphatic hydrocarbons, aralkyl hydrocarbons, and their substituted derivatives, e.g., substituted with methyl, ethyl, cyclopentyl, benzyl, etc.

Suitable aromatic moieties include, but are not limited to, monocyclic, polycyclic and fused aromatic compounds having from 6 to 30, and preferably from 6 to 18 ring carbon atoms, and their substituted derivatives. Polycyclic aromatic moieties may be directly linked (such as, for example, biphenyl) or may be separated by 1 or 2 atoms comprising linking moieties. Illustrative non-limiting examples of aromatic moieties include phenyl, biphenyl, naphthyl, and their substituted derivatives. In addition, in some embodiments, $G_n$ can include structures which are part of another fused ring including, but not limited to, The ortho steric effects may also be extended to other bisaromatic diamines to examine if there is a similar effect on increasing the polymers' thermal properties (e.g., Tg). In addition, other positions on the ring may be substituted with the same substituents described above for G.

Preferred substituents include one or more aromatic groups, preferably phenyl groups, alkoxy or aryloxy groups, their sulfur analogues, halogen-substituted phenyl groups, or mixtures thereof.

The production of the bis(halophthalimide) preferably occurs in the presence of a non-polar organic liquid, usually having a substantially lower polarity than that of the dipolar aprotic solvents such as dimethylformamide, dimethylacetamide and N-methylpyrrolidinone. Said non-polar solvent preferably has a boiling point above about 100° C. and most preferably above about 150° C., in order to facilitate the reaction which requires temperatures above that temperature. Suitable liquids of this type include o-dichlorobenzene, dichlorotoluene, 1,2,4-trichlorobenzene, diphenyl sulfone and alkoxybenzenes such as anisole and veratrole, and more generically liquids whose polarity is no higher than those of the aforementioned liquids. Liquids of similar polarity but lower boiling points, such as chlorobenzene, may be employed at super-atmospheric pressures. Anisole and o-dichlorobenzene are usually preferred.

The bis(halophthalimide) preparation method of the invention typically employs temperatures of at least 110° C., preferably in the range from 150° to about 275° C., preferably about 175–225° C. At temperatures below 110° C., reaction rates are for the most part too slow for economical operation. It is within the scope of the invention to employ super-atmospheric pressures, typically up to about 5 atm, to facilitate the use of high temperatures without causing liquid to be lost by evaporation through boiling.

A further feature, for the same reason, is a solids content in the reaction mixture of at least about 5%, preferably at least about 12% and most preferably about 15–25%, by weight. By "solids content" is meant the proportion of bishalophthalimide product as a percentage of the total weight of the bishalophthalimide and solvent. It is further within the scope of the invention to change the solids content during the reaction, for such reasons as to effectuate transfer of the reaction mixture from one vessel to another.

Other constituent proportions in the reaction mixture preferably include, a molar ratio of anhydride to diamine in the range of from about 1.98:1 to about 2.04:1, with a ratio of about 2:1 being most preferred. While other ratios may be employed, a slight excess of anhydride or diamine may be desirable. Catalyst, if used, is present in an amount effective to accelerate the reaction, usually about 0.1–0.3% by weight based on the weight of diamine. Suitable imidization catalysts include, but are not limited to, sodium phenyl phosphinate, acetic acid, benzoic acid, phthalic acid, or substituted derivatives thereof. In one embodiment, sodium phenyl phosphinate is utilized as the imidization catalyst.

The reaction between at least one amine reactant and at least one anhydride reactant by the methods of the present invention results in products generally comprising phthalimides of formula (I). Bis(halophthalimides) similar to formula (I) which may be produced from substituted 1,3-diamines include bis[N-(3-chlorophalimide)] derivatives of diamines such as 2,4-bis[N-(3-chlorophthalimido)]toluene, 2,6-bis[N-(3-chlorophthalimido)]toluene, 2,4-bis[N-(3-chlorophthalimido)]-3,5-diethyltoluene, 2,6-bis[N-(3-chlorophthalimido)]-3,5-diethyltoluene and the corresponding chloro, bromo and nitro compounds. Mixtures of such compounds may also be employed. Where the starting phthalic anhydride is pure 3-ClPA, a 3-3'-ClPAMI as depicted in reaction scheme (II) is produced and then subsequently reacted with additional components to produce the desired polyetherimide. However, as noted above, in other embodiments a mixture of 3-ClPA with other phthalic anhydrides, including 4-ClPA, dichlorophthalic anhydride, and phthalic anhydride, may be utilized to produce the desired halophthalimide which, in turn, is then utilized to produce the desired polyetherimide.

At least one dihydroxy-substituted aromatic hydrocarbon is then reacted with the ClPAMI to produce the desired polyetherimide. Suitable dihydroxy-substituted aromatic hydrocarbons include those having the formula

HO-A²-OH,   (IV)

wherein A² is a divalent aromatic hydrocarbon radical. Suitable A² radicals include m-phenylene, p-phenylene, 4,4'-biphenylene, 4,4'-bi(3,5-dimethyl)phenylene, 2,2-bis(4-phenylene)propane and similar radicals such as those which correspond to the dihydroxy-substituted aromatic hydrocarbons disclosed by name or formula (generic or specific) in U.S. Pat. No. 4,217,438.

The A² radical preferably has the formula

-A³-Y-A⁴-,   (V)

wherein each of A³ and A⁴ is a monocyclic divalent aromatic hydrocarbon radical and Y is a bridging hydrocarbon radical in which one or two atoms separate A³ from A⁴. The free valence bonds in formula V are usually in the meta or para positions of A³ and A⁴ in relation to Y. Compounds in which A² has formula V are bisphenols, and for the sake of brevity the term "bisphenol" is sometimes used herein to designate the dihydroxy-substituted aromatic hydrocarbons; it should be understood, however, that non-bisphenol compounds of this type may also be employed as appropriate.

In formula V, the A³ and A⁴ values may be unsubstituted phenylene or halo or hydrocarbon-substituted derivatives thereof, illustrative substituents (one or more) being alkyl, alkenyl, bromo, chloro. Unsubstituted phenylene radicals are preferred. Both A³ and A⁴ are preferably p-phenylene, although both may be o- or m-phenylene or one o- or m-phenylene and the other p-phenylene.

The bridging radical, Y, is one in which one or two atoms, preferably one, separate A³ from A⁴. Illustrative radicals of this type are methylene, cyclohexylmethylene, 2-[2.2.1]-bicycloheptylmethylene, ethylene, isopropylidene, neopentylidene, cyclohexylidene, cyclopentadecylidene, cyclododecylidene and adamantylidene; gem-alkylene (alkylidene) radicals are preferred. Also included, however, are unsaturated radicals.

Some preferred examples of dihydric phenols which may be utilized include 6-hydroxy-1-(4'-hydroxyphenyl)-1,3,3-trimethylindane, 4,4'-(3,3,5-trimethylcyclo-hexylidene) diphenol; 1,1-bis(4-hydroxy-3-methylphenyl)cyclohexane; 2,2-bis(4-hydroxyphenyl)propane (commonly known as bisphenol-A); 2,2-bis(4-hydroxy-3,5-dimethylphenyl) propane; 2,2-bis(4-hydroxy-3-methylphenyl)propane; 2,2-bis(4hydroxy-3-ethylphenyl)propane; 2,2-bis(4-hydroxy-3-isopropylphenyl)propane; 2,4'-dihyroxydiphenylmethane; bis(2-hydroxyphenyl)methane; bis(4-hydroxy-phenyl) methane; bis(4-hydroxy-5-nitrophenyl)methane; bis(4-hydroxy-2,6-dimethyl-3-methoxyphenyl)methane; 1,1-bis(4-hydroxyphenyl)ethane; 1,1-bis(4-hydroxy-2-chlorophenyl)ethane; 2,2-bis(3-phenyl-4-hydroxyphenyl)-propane; bis(4-hydroxyphenyl)cyclohexylmethane; 2,2-bis(4-hydroxyphenyl)-1-phenylpropane; resorcinol; $C_{1-3}$ alkyl-substituted resorcinols. For reasons of availability and particular suitability for the purposes of this invention, in one embodiment the preferred dihydric phenol is bisphenol A in which the radical of formula V is the 2,2-bis(4-phenylene)propane radical and in which Y is isopropylidene and A³ and A⁴ are each p-phenylene.

Preferably, the reaction of salts of dihydroxyaromatic compounds are utilized in the methods of the present disclosure. More preferably, alkali metal salts of dihydroxy-substituted aromatic hydrocarbons are employed. These alkali metal salts are typically sodium or potassium salts, with sodium salts frequently preferred by reason of their availability and relatively low cost. Most preferably, bisphenol A disodium salt (BPA.NA₂) is utilized.

In a preferred embodiment, bisphenol A disodium salt is added to the organic solvent and the mixture azeotroped to a dry condition. Then, a second co-monomer, for example a bis[N-(3-chlorophthalimide)] of a 1,3-diamine, may be added and the mixture azeotroped to a dry condition. Then a catalyst may be added as a pre-dried solution in organic solvent. The process is expedited when predried solvent and co-monomers are used. Preferably, the molar ratio of bisphenol A disodium salt to the bis[N-(3-chlorophthalimide)] of a 1,3-diamine, e.g., 1,3 bis[N-(3-chlorophtalimido)]toluene, ranges from about 1.0:0.9 to 0.9:1.0.

One class of preferred solvents utilized in producing the polyetherimide includes those of low polarity. Suitable solvents of this type include halogenated aromatic compounds such as o-dichlorobenzene, dichlorotoluene and 1,2,4-trichlorobenzene; and diphenyl sulfone. Solvents of similar polarity but lower boiling points, such as chlorobenzene, may be employed at superatmospheric pressures. Another class of preferred solvents includes aromatic ethers such as diphenyl ether, phenetole (ethoxybenzene), and anisole (methoxybenzene). O-dichlorobenzene and alkoxybenzenes, most preferably anisole, are particularly preferred. In many instances, halogenated aromatic solvents are preferred over alkoxybenzenes since the former have less tendency than the latter to interact with and inactivate the phase transfer catalyst described below. Another class of solvents suitable for the present invention is polar aprotic solvents, illustrative examples of which include dimethylformamide (DMF), dimethylacetamide (DMAc), dimethylsulfoxide (DMSO), and N-methylpyrrolidinone (NMP).

The preferred phase transfer catalysts, by reason of their exceptional stability at high temperatures and their effectiveness to produce high molecular weight aromatic polyether polymers in high yield are the hexaalkylguanidinium and α,ω-bis(pentaalkylguanidinium)alkane salts. For the sake of brevity, both types of salts are hereinafter sometimes designated "guanidinium salt".

Suitable guanidinium salts are illustrated by those of the formula

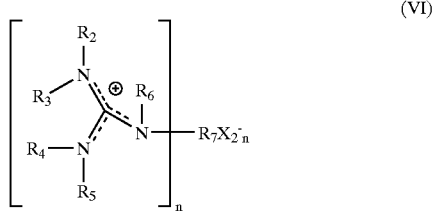

(VI)

wherein:

each of $R^2$, $R^3$, $R^4$, $R^5$ and $R^6$ is a primary alkyl radical and $R^7$ is a primary alkyl or bis(primary alkylene) radical, or at least one of the $R^2$—$R^3$, $R^4$—$R^5$ and $R^6$—$R^7$ combinations with the connecting nitrogen atom forms a heterocyclic radical;

$X^2$ is an anion; and n is 1 or 2.

The alkyl radicals suitable as $R^{2-6}$ include primary alkyl radicals, generally containing about 1–12 carbon atoms. $R^7$ is usually an alkyl radical of the same structure as $R^{2-6}$ or a $C_{2-12}$ alkylene radical in which the terminal carbons are primary; most preferably, it is $C_{2-6}$ alkyl or $C_{4-8}$ straight chain alkylene. Alternatively, any combination of $R^{2-7}$ and the corresponding nitrogen atom(s) may form a heterocyclic radical such as piperidino, pyrrolo or morpholino.

The $X^2$ value may be any anion and is preferably an anion of a strong acid; examples are chloride, bromide and methanesulfonate. Chloride and bromide ions are usually preferred. The value of n will be 1 or 2 depending on whether $R^7$ is alkyl or alkylene.

As can be seen in formula VI, the positive charge in the guanidinium salt is delocalized over one carbon and three nitrogen atoms. This is believed to contribute to the salts' stability under the relatively high temperature conditions encountered in embodiments of the invention.

Additionally, the reaction is typically sensitive to water and it is preferable to dry the solvent-comprising reaction mixture by known methods, for example by boiling or azeotroping water from the mixture, typically prior to delivering the catalyst. In one embodiment, water removal from the system can be accomplished in either batch, semicontinuous or continuous processes using means well-known in the art such as a distillation column in conjunction with one or more reactors. In one embodiment, a mixture of water and non-polar organic liquid distilling from a reactor is sent to a distillation column where water is taken off overhead and solvent is recycled back into the reactor at a rate to maintain or increase the desired solids concentration. Other methods for water removal include, but are not limited to, passing the condensed distillate through a drying bed for chemical or physical adsorption of water.

Without wishing to be bound by any theory, it is believed the sterically hindered substituted 1,3-aromatic diamines restricts rotation of the imide ring around the C—N bond of attachment to the diamine ring, thus preventing the bisimide molecule from assuming the coplanarity and structure conducive to the formation of cyclic oligomers, especially the 1:1 monocyclic adduct. By reducing the amount of cyclic oligomer, the unfavorable interaction between the imide carbonyl/s and the adjacent alkyl group/s is avoided.

While the present disclosure has focused on 1,3-diamines, other diamines may be substituted with compounds which result in sterically hindered diamines which, in turn, may be utilized in forming monomers that are polymerized to produce polyetherimides. The resulting polyetherimides have lower levels of cyclic by-products than polymers obtained by using nonsubstituted monomers.

Polyetherimide resins produced in accordance with the methods of the present disclosure have improved thermomechanical performance characteristics such as glass transition temperature (Tg) or heat deflection temperature (HDT).

The present disclosure is illustrated by the following non-limiting examples.

EXAMPLE 1

ClPAMI monomers were prepared from 3-ClPA and substituted 1,3-diamines. The substituted 1,3-diamines utilized were as follows: 2,4-toluene diamine (2,4-TDA), 2,6-toluene diamine (2,6-TDA), and diethyl toluene diamine (Ethacure 100). m-phenylene diamine (mPD) is the parent unsubstituted 1,3-diamine. p-Phenylene diamine (pPD), diaminodiphenyl sulfones (3,3'-DDS and 4,4'-DDS) and 4,4'-oxydianiline (ODA) were included for comparison.

The results of the solid analysis and solubility obtained with substituted 1,3-diamines used in the synthesis of ClPAMI monomers are outlined in Table 1 below.

The % solids in the ClPAMI monomers prepared from these various diamines was determined by dividing the theoretical weight of the sample by the weight of the sample and solvent.

The solubility of the ClPAMI monomers was determined visually as the product being completely soluble at the specific % solids indicated at the boiling point of the solvent (o-DCB at 180° C.). Otherwise solubility was low or the monomer was sparingly soluble.

TABLE 1

Synthesis of ClPAMI monomers from 3-ClPA

| | Diamine | Ex. 1 mPD | Ex. 2 2,4-TDA | Ex. 3 2,6-TDA | Ex. 4 Ethacure 100 | Comp. Ex. 1 pPD | Comp. Ex. 2 ODA | Comp. Ex. 3 3,3'-DDS | Comp. Ex. 4 4,4'-DDS |
|---|---|---|---|---|---|---|---|---|---|
| ClPAMI | | | | | | | | | |
| % Solids | | 20 | 30 | 39 | 40 | 20 | 35 | 33 | 30 |
| Solubility | | Low | Soluble | Soluble | Soluble | Sparingly | Soluble | Soluble | Low |

Ethacure 100 is ~80% 3,5-Diethyl-2,4-toluenediamine and ~20% 3,5-Diethyl-2,6-toluenediamine commercially available from Albemarle ® Corporation.

As is apparent from the above example, the ClPAMI monomers prepared with 2,4-toluene diamine, 2,6-toluene diamine, and diethyl toluene diamine had enhanced solubility compared with the mPD and pPD.

EXAMPLE 2

ClPAMI monomers produced in accordance with the methods set forth above in Example 1 were then utilized to produce polyetherimides. The glass transition temperature (Tg) of each resin were obtained were obtained by Differential Scanning Calorimetry using a Perkin Elmer DSC7 machine. The % cyclic monomer and % total cyclics were determined by Gel Permeation Chromatography (GPC). GPC analysis was performed by using chloroform as eluent (elution rate of 0.8 ml·min−1) on a HP 1100 Series apparatus equipped with a PL gel 5 um Mixed-C column and a UV detector utilizing the manufacturer's software. Elution rate on 0.7 mL/min on a Polymer Labs HT-120 GPC system equipped with a PL gel Mixed-C column and UV detector, utilizing Perkin Elmer Turbochrom software.

The results, set forth below in Table 2, demonstrate that ClPAMI monomers produced with substituted 1,3-diamines gave polyetherimides having lower levels of cyclics with comparable or better glass transition temperatures.

TABLE 2

Synthesis and cyclics reduction in 3-ClPA/1,3-diamines/BPA Polymers

|  | Ex. 1 mPD | Ex. 2 2,4-TDA | Ex. 3 2,6-TDA | Ex. 4 80:20 TDA* | Ex. 5 Ethacure | Comp. Ex. 2 ODA | Comp. Ex. 3 3,3'-DDS | Comp. Ex. 4 4,4'-DDS |
|---|---|---|---|---|---|---|---|---|
| Diamine |  |  |  |  |  |  |  |  |
| Polymer Property |  |  |  |  |  |  |  |  |
| Tg (C) | 231 | 245 | 255 | 247 | 265 | 235 | 226 | 263 |
| % Cyclic Monomer | 10.4 | 1.5 | 3.1 | 1.02 | 1.3 | 0.07 | 1.23 | 0.04 |
| % Total Cyclics | 13.2 | 3.37 | 5.3 | 2.43 | 2.9 | 1.2 | 2.1 | 1.65 |

*80% 2,4-TDA and 20% 2,6-TDA

The above results clearly indicate that simple, relatively cheap and commercially available substituted 1,3-diamines are surprisingly capable of providing a good balance of performance benefits ranging from ease of ClPAMI synthesis, reduction of formation of cyclics, and good thermal performance (Tg), all of which can occur at reduced cost.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method for preparing a bis(halophthalimide) which comprises combining at a temperature of at least 110° C.:
   at least one halophthalic anhydride;
   a 1,3-diamine having at least one substituent ortho to one of its amine functionalities;
   an organic liquid having a polarity no higher than that of o-dichlorobenzene, dichlorotoluene, 1,2,4-trichlorobenzene, diphenyl sulfone, anisole and veratrole; and
   obtaining the bis(halophthalimide).

2. The method of claim 1 wherein the combining step further comprises combining at least one halophthalic anhydride selected from the group consisting of substantially pure 3-chlorophthalic anhydride and 3-chlorophthalic anhydride combined with another phthalic anhydride selected from the group consisting of 4-chlorophthalic anhydride, dichlorophthalic anhydride, phthalic anhydride, and mixtures thereof.

3. The method of claim 1 wherein the combining step further comprises combining a 1,3 diamine of the formula

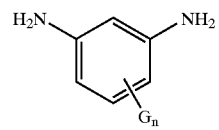

where n is 1 to 4, G is selected from the group consisting of —R, —OR, —SR, —Ar, —OAr, —SAr, and —CN, and R is selected from the group consisting of $C_1$ to $C_{30}$ aliphatic hydrocarbons, $C_1$ to $C_{30}$ unsaturated cycloaliphatic hydrocarbons, and aralkyl hydrocarbons.

4. The method of claim 1 wherein the combining step further comprises combining anhydride to diamine at a molar ratio of from about 1.98:1 to about 2.04:1.

5. The method of claim 1 wherein the combining step further comprises combining anhydride to diamine at a molar ratio of about 2:1.

6. The method of claim 1 wherein the combining step further comprises combining an organic liquid selected from the group consisting of o-dichlorobenzene and anisole.

7. The method of claim 1 wherein the combining step further comprises combining 3-chlorophthalic anhydride with the 1,3-diamine and the organic liquid.

8. The method of claim 1 further wherein the combining step further comprises combining an imidization catalyst with the at least one halophthalic anhydride, the 1,3-diamine, and the organic liquid.

9. The method of claim 8 wherein the combining step further comprises combining an imidization catalyst selected from the group consisting of sodium phenyl phosphinate, acetic acid, benzoic acid, and phthalic acid.

10. The method of claim 1 wherein the combining step further comprises combining a phthalic anhydride to produce a halophthalimide capable of acting as an end-capping monomer.

11. A method for preparing a bis[N-(3-chlorophthalimide)] derivative of a diamine made by contacting at a temperature of at least 110° C. a 3-chlorophthalic anhydride with a 1,3-diamine having at least one substituent ortho to one of its amine functionalities in the presence of an organic liquid having a polarity no higher than that of o-dichlorobenzene, dichlorotoluene, 1,2,4-trichlorobenzene, diphenyl sulfone, anisole and veratrole.

12. The method of claim 11 wherein the combining step further comprises combining the 3-chlorophthalic anhydride with another phthalic anhydride selected from the group consisting of 4-chlorophthalic anhydride, dichlorophthalic anhydride, phthalic anhydride, and mixtures thereof.

13. The method of claim 11 wherein the combining step further comprises combining a 1,3 diamine of the formula

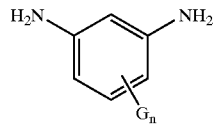

where n is 1 to 4, G is selected from the group consisting of —R, —OR, —SR, —Ar, —OAr, —SAr, and —CN, and R is selected from the group consisting of $C_1$ to $C_{30}$ aliphatic hydrocarbons, $C_1$ to $C_{30}$ unsaturated cycloaliphatic hydrocarbons, and aralkyl hydrocarbons.

14. The method of claim 11 wherein the combining step further comprises combining the anhydride to the diamine at a molar ratio of from about 1.98:1 to about 2.04:1.

15. The method of claim 11 wherein the combining step further comprises combining the anhydride to the diamine at a molar ratio of about 2:1.

16. The method of claim 11 wherein the combining step further comprises combining an organic liquid selected from the group consisting of o-dichlorobenzene and anisole.

17. The method of claim 11 wherein the bis[N-(3-chlorophthalimide)] derivative is selected from the group consisting of 2,4-bis[N-(3-chlorophthalimido)]toluene, 2,6-bis[N-(3-chlorophthalimido)]toluene, 2,4-bis[N-(3-chlorophthalimido)]-3,5-diethyltoluene, and 2,6-bis[N-(3-chlorophthalimido)]-3,5-diethyl toluene.

18. A method for preparing an aromatic polyether polymer which comprises combining the bis[N-(3-chlorophthalimide)] derivative of a diamine produced in accordance with the method of claim 11 with at least one alkali metal salt of a dihydroxy-substituted aromatic compound in the presence of a phase transfer catalyst, and obtaining a polyether polymer wherein the resulting polyether polymer has reduced levels of cyclic oligomer by-products.

19. The method of claim 18 wherein the combining step further comprises combining a phase transfer catalyst selected from the group consisting of hexaalkylguanidinium alkane salts and α,ω-bis(pentaalkylguanidinium)alkane salts.

20. The method of claim 18 wherein the combining step further comprises combining bisphenol A disodium salt with the bis[N-(3-chlorophthalimide)] derivative of a diamine.

21. The method of claim 18 wherein the bis[N-(3-chlorophthalimide)] derivative is selected from the group consisting of 2,4-bis[N-(3-chlorophthalimido)]toluene, 2,6-bis[N-(3-chlorophthalimido)]toluene, 2,4-bis[N-(3-chlorophthalimido)]-3,5-diethyltoluene, and 2,6-bis[N-(3-chlorophthalimido)]-3,5-diethyl toluene.

22. The method of claim 18 wherein the combining step further comprises combining hexaalkylguanidinium chloride as the phase transfer catalyst.

23. A method for preparing a polyetherimide which comprises combining a bisphenol A disodium salt;

a bis[N-(3-chlorophthalimide)] derivative of a diamine;

a diluent selected from the group consisting of o-dichlorobenzene and anisole;

a catalytically active amount of a phase transfer catalyst; and obtaining a polyetherimide, wherein said bis[N-(3-chlorophthalimide)] derivative comprises the reaction product of a mixture comprising a 3-chlorophthalic anhydride; a 1,3 diamine of the formula

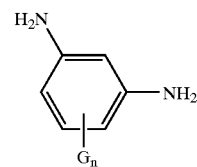

where n is 1 to 4, G is selected from the group consisting of —R, —OR, —SR, —Ar, —OAr, —SAr, and —CN, and R is selected from the group consisting of $C_1$ to $C_{30}$ aliphatic hydrocarbons, $C_1$ to $C_{30}$ unsaturated cycloaliphatic hydrocarbons, and aralkyl hydrocarbons.

24. The method of claim 23 wherein the bis[N-(3-chlorophthalimide)] derivative is selected from the group consisting of 2,4-bis[N-(3-chlorophthalimido)]toluene, 2,6-bis[N-(3-chlorophthalimido)]toluene, 2,4-bis[N-(3-chlorophthalimido)]-3,5-diethyltoluene, and 2,6-bis[N-(3-chlorophthalimido)]-3,5-diethyl toluene.

25. The method of claim 23 wherein the combining step further comprises combining the phase transfer catalyst selected from the group consisting of hexaalkylguanidinium alkane salts and α,ω-bis(pentaalkylguanidinium)alkane salts.

26. The method of claim 23 wherein the combining step further comprises combining hexaalkylguanidinium chloride as the phase transfer catalyst.

* * * * *